United States Patent [19]
Esler

[11] Patent Number: 6,128,529
[45] Date of Patent: *Oct. 3, 2000

[54] DEVICE AND METHOD PROVIDING PACING AND ANTI-TACHYARRHYTHMIA THERAPIES

[75] Inventor: James A. Esler, Columbia Heights, Minn.

[73] Assignee: Cardiac Pacemakers, Inc., St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/790,908

[22] Filed: Jan. 29, 1997

[51] Int. Cl.$^7$ .................................................. A61N 1/39
[52] U.S. Cl. ................................................................ 607/4
[58] Field of Search ......................................... 607/4, 9, 14

[56] References Cited

U.S. PATENT DOCUMENTS

| | | | |
|---|---|---|---|
| 4,378,020 | 3/1983 | Nappholz et al. | 607/9 |
| 4,407,288 | 10/1983 | Langer et al. | 607/4 |
| 4,523,593 | 6/1985 | Rueter | 607/9 |
| 4,951,667 | 8/1990 | Markowitz et al. | 607/14 |
| 5,048,521 | 9/1991 | Pless et al. | 607/9 |
| 5,161,527 | 11/1992 | Nappholz et al. | 607/4 |
| 5,205,283 | 4/1993 | Olson | 607/4 |

OTHER PUBLICATIONS

Hayes, D.L., et al., "Pacemaker Timing Cycles", *Cardiac Pacing*, Edited by Kenneth A. Ellenbogen, M.D., published by Blackwell Science, pp. cover page, title page and 263–308 (1992).

*Primary Examiner*—William E. Kamm
*Assistant Examiner*—George R. Evanisho
*Attorney, Agent, or Firm*—Schwegman, Lundberg, Woessner & Kluth, P.A.

[57] ABSTRACT

Recognizing that delivery of pacing therapy to a patient may increase the risk of inappropriate delivery of anti-tachyarrhythmia therapy, a modified atrial-based timing device and method delivers pacing and anti-tachyarrhythmia therapy to the patient such that the risk is reduced. A ventricular-atrial (VA) time interval is increased, when an intrinsic ventricular activation is sensed during an atrial-ventricular (AV) time interval, by the time remaining in the immediately preceding AV time interval following the intrinsic ventricular activation sensed therein. As a result, the patient's heart rate is not elevated, in response to ventricular activations sensed during the AV time interval, and a tachyarrhythmia rate threshold is not exceeded, thereby avoiding inappropriate delivery of anti-tachyarrhythmia therapy.

25 Claims, 7 Drawing Sheets

DEVICE AND METHOD PROVIDING PACING AND ANTI-TACHYARRHYTHMIA THERAPIES

TECHNICAL FIELD OF THE INVENTION

This invention relates generally to cardiac rhythm management devices and methods and particularly to an automatic implantable cardioverter-defibrillator providing pacing and anti-tachyarrhythmia therapy.

BACKGROUND OF THE INVENTION

Cardiac arrhythmias have traditionally been segregated, for treatment by drug therapy or a cardiac rhythm management device, into bradyarrhythmias and tachyarrhythmias. Patients having certain bradyarrhythmias that are not responsive to drug therapy are often possible candidates for an implantable pacemaker device to provide electrical pacing stimuli to manage their irregular and abnormally slow cardiac rhythms. Patients having certain tachyarrhythmias that are not responsive to drug therapy are often possible candidates for an implantable cardioverter-defibrillator device to provide anti-tachyarrhythmia therapy, such as low-energy cardioversion countershock therapy or higher-energy defibrillation countershock therapy, to manage their irregular and abnormally fast cardiac rhythms. Other cardiac rhythm management devices incorporate anti-tachycardia pacing for converting a tachyarrhythmia into a normal cardiac rhythm.

A particular concern in cardioverter-defibrillators is avoiding the delivery of inappropriate countershock therapy in the absence of heart activity indicative of a need for such therapy. Because of the significant energy levels typically used in cardioversion and defibrillation countershocks, patients typically experience a significant degree of fright and discomfort if such therapy is delivered inappropriately. This may, in turn, put the patient at risk of other injuries arising from whatever activity the patient is engaged in when the inappropriate therapy is received. Repeated instances of inappropriate countershock therapy may also deplete the power source of the implantable cardioverter-defibrillator, reducing the implanted longevity over which the device is effective at providing anti-tachyarrhythmia therapy. Moreover, the inappropriate delivery of countershock therapy increases the difficulty for the physician in properly diagnosing and treating the cardiac patient.

Countershock therapy may itself pose certain adverse side-effects. A countershock may temporarily degrade cardiac function, resulting in a period of ischemia. A countershock may increase myocardial irritability, leaving the patient in a state of increased susceptibility to induction of tachyarrhythmias, including fibrillation. Actual post-countershock arrhythmias may also result. Because of the risks inherent in countershock therapy, its inappropriate delivery should be avoided whenever possible. Other anti-tachyarrhythmia therapies also have certain inherent risks. For example, anti-tachycardia pacing therapy includes a risk of inducing and accelerating certain tachyarrhythmias, including life-threatening ventricular fibrillation. Because of the risks arising from such anti-tachyarrhythmia therapy, its inappropriate delivery should also be avoided whenever possible.

Certain patients have cardiac arrhythmias requiring both pacing therapy for bradyarrhythmic episodes, and anti-tachyarrhythmia therapy for tachyarrhythmic episodes. One problem in that is particularly troublesome in cardiac rhythm management devices providing both pacing and anti-tachyarrhythmia therapy, is that delivery of the pacing therapy may increase the risk of delivering an inappropriate countershock under certain conditions. Because of the above-described risks inherent in delivering inappropriate anti-tachyarrhythmia therapy, there is a need in the art for a cardiac rhythm management device, such as an implantable cardioverter-defibrillator, that provides both pacing and anti-tachyarrhythmia therapies without exacerbating such risks by the delivery of pacing or other bradyarrhythmia therapy.

SUMMARY OF THE INVENTION

The present invention recognizes that the delivery of pacing therapy may, under certain conditions, result in inappropriate delivery of anti-tachyarrhythmia therapy. The present invention includes a modified atrial-based timing device and method that provides pacing and anti-tachyarrhythmia therapies to the heart such that the risk of inappropriate delivery of anti-tachyarrhythmia therapy is advantageously reduced.

In the method of the present invention, an atrial-ventricular (AV) time interval is initiated upon an atrial event. Heart activity is sensed during the AV time interval. The sensing of heart activity includes the sensing of a ventricular activation during the AV time interval. A determination is made of the time remaining in the AV time interval subsequent to the ventricular activation sensed during the AV time interval. A ventricular-atrial (VA) time interval is lengthened by the time remaining in the AV time interval, i.e. lengthened by the difference in time between the occurrence of the sensed ventricular activation and the time at which a ventricular pacing pulse would have been delivered had no ventricular activation been sensed during the AV time interval. A determination is made whether the sensed heart activity indicates a need for anti-tachyarrhythmia therapy. Anti-tachyarrhythmia therapy is delivered if the sensed heart activity indicates a need for anti-tachyarrhythmia therapy.

The invention also provides a cardiac rhythm management device, that includes an interface circuit that conveys signals, including a heart activity signal, between the device and a heart. The device also includes a microcontroller that initiates an atrial-ventricular (AV) time interval upon an atrial event and a ventricular-atrial (VA) time interval upon a ventricular event. The microcontroller lengthens the VA time interval in response to a sensed ventricular event, such as when the heart activity signal including a ventricular activation sensed during the AV time interval. The device also includes an anti-tachyarrhythmia therapy circuit that provides anti-tachyarrhythmia therapy to the heart.

Thus, the present invention reduces the risk of delivering inappropriate anti-tachyarrhythmia therapy by providing a modified atrial-based timing device and method that provides pacing and anti-tachyarrhythmia therapies to the heart.

BRIEF DESCRIPTION OF THE DRAWINGS

In the drawings, like numerals describe substantially similar components throughout the several views.

DETAILED DESCRIPTION OF THE INVENTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
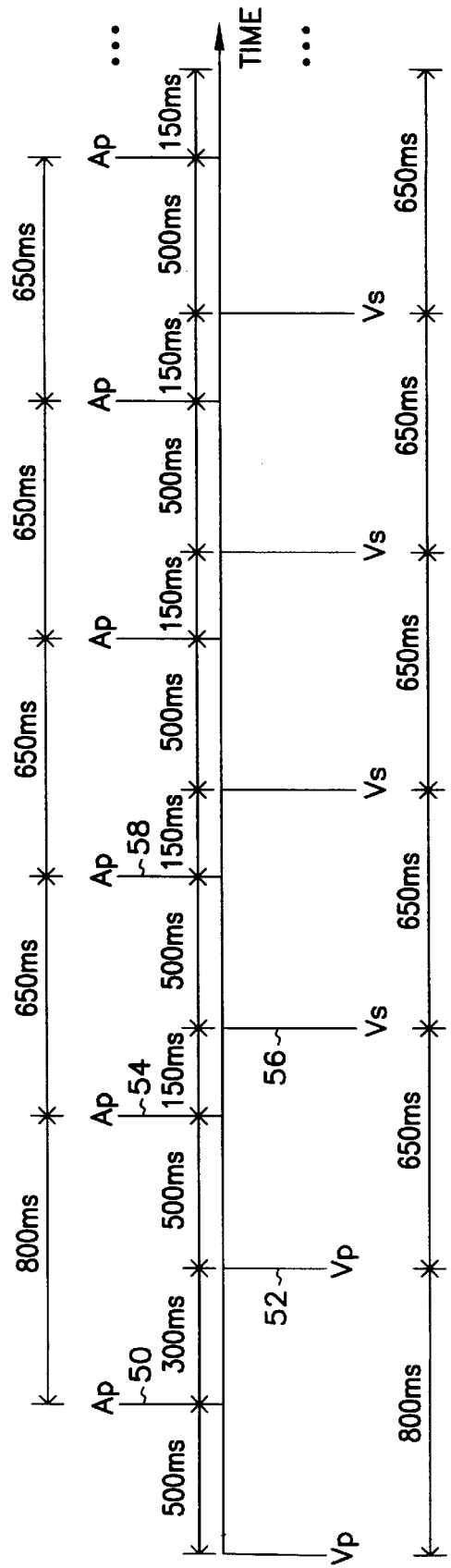
FIG. 1 is a timing diagram illustrating paced and sensed events in a scenario illustrating a problem faced by a typical defibrillators with DDD pacing capability.

FIG. 1 is a timing diagram including a scenario that illustrates a problem faced by a defibrillator with pacing capability. FIG. 1 includes both paced and sensed events. The paced events include pacing stimuli, such as electrical pulses, that are provided to the atrium or ventricle of the heart to cause depolarizations therein. The sensed events include intrinsic activations that are sensed in the atrium or ventricle of the heart and cause depolarizations therein. In FIG. 1, atrial events are illustrated as extending upward from the horizontal time axis, and are designated with an "A". Ventricular events are illustrated as extending downward from the horizontal time axis, and are designated with a "V". Paced events are designated with a "p" subscript, and sensed events are designated with a "s" subscript.

In the example of FIG. 1, the defibrillator mode of operation is programmed to provide both atrial and ventricular pacing and sensing, and the response to a sensed atrial or ventricular activation is programmed to inhibit delivery of a pacing pulse to the chamber in which the activation is sensed; this defibrillator mode of operation is referred to as DDD mode, and a defibrillator having such a mode of operation is referred to as having DDD pacing capability. The defibrillator is programmed to provide pulses to a particular chamber of the heart at a rate of 75 beats per minute, which corresponds to an 800 millisecond time interval between pulses to the particular chamber of the heart. The defibrillator is also programmed to have an atrial-ventricular (AV) time interval of 300 milliseconds, i.e. delivery of a ventricular pacing pulse is delayed from delivery of the atrial pacing pulse or sensed atrial event by the AV time interval of 300 milliseconds.

The example of FIG. 1 illustrates a defibrillator having DDD pacing capability in which a fixed ventricular-atrial (VA) interval is used. The fixed VA interval is defined by the difference between the time interval that corresponds to the heart rate and the AV time interval. In the example of FIG. 1, a fixed VA time interval of 500 milliseconds is defined by the difference between the time interval that corresponds to the programmed heart rate (800 milliseconds) and the AV time interval (300 milliseconds). The defibrillator is also programmed to inhibit delivery of a pacing pulse when an intrinsic activation of the heart is sensed.

In FIG. 1, a first pulse 50 is delivered to the atrium, thereby also initiating a 300 millisecond AV time interval. A second pulse 52 is delivered to the ventricle 300 milliseconds later, since no ventricular activation was sensed during the AV time interval initiated by first pulse 50. The delivery of second pulse 52 also initiates a 500 millisecond VA time interval. A third pulse 54 is delivered to the atrium 500 milliseconds later, since no atrial activation was sensed during the VA time interval initiated by second pulse 52. Subsequent events in the timing diagram of FIG. 1 illustrate a possible condition in which electrical conduction, through physiological pathways from the atrium to the ventricle, is faster than the 300 millisecond AV time interval.

For example, with such fast conduction between the atrium and the ventricle, the delivery of third pulse 54 may result in a conducted intrinsic first ventricular activation 56 that is sensed 150 milliseconds after third pulse 54, i.e. during the 300 millisecond AV time interval initiated by third pulse 54. In the defibrillator of this example, the sensed ventricular activation inhibits the delivery of any ventricular pacing pulse, and also initiates a subsequent fixed 500 millisecond VA time interval. Upon the expiration of the VA time interval, an atrial fourth pace pulse 58 is delivered.

FIG. 1 illustrates the possibility of similar subsequent sensed ventricular events, each occurring within the 300 millisecond AV time interval initiated by the previous atrial pace pulse, due to the fast electrical conduction between the atrium and ventricle of the heart. This results in an elevated heart rate of 92 beats per minute for these subsequent events, corresponding to a time interval of 650 milliseconds between atrial events or between ventricular events.

Fast atrial-ventricular conduction may result from physiological pathways, such as may be present within the defibrillator patient population, or may also result from an inappropriately long AV time interval programmed by the physician. In any case, the potential for elevated heart rates increases the risk of inappropriate delivery of antitachyarrhythmia therapy. If the elevated heart rate reaches a tachyarrhythmia rate threshold, delivery of antitachyarrhythmia therapy, such as an electrical countershock, may be triggered as a result. In such a case, the condition that is interpreted as a tachyarrhythmia does not result from intrinsic heart activity; it results instead from an artificially elevated heart rate condition caused by the delivery of pacing therapy, sometimes referred to as a form of pacemaker mediated tachycardia (PMT). In such a case, the delivery of anti-tachyarrhythmia therapy is unneeded and inappropriate.

The present invention provides a cardiac rhythm management system that includes a device and method for providing pacing and anti-tachyarrhythmia therapies to the heart such that the risk of inappropriate delivery of antitachyarrhythmia therapy is reduced. One aspect of the present invention, is the recognition that delivery of pacing therapy may, under certain conditions, result in inappropriate delivery of anti-tachyarrhythmia therapy. The system minimizes the risk of inappropriate delivery of antitachyarrhythmia therapy by providing a modified atrial-based timing apparatus and method, as described below.

Figure 2:
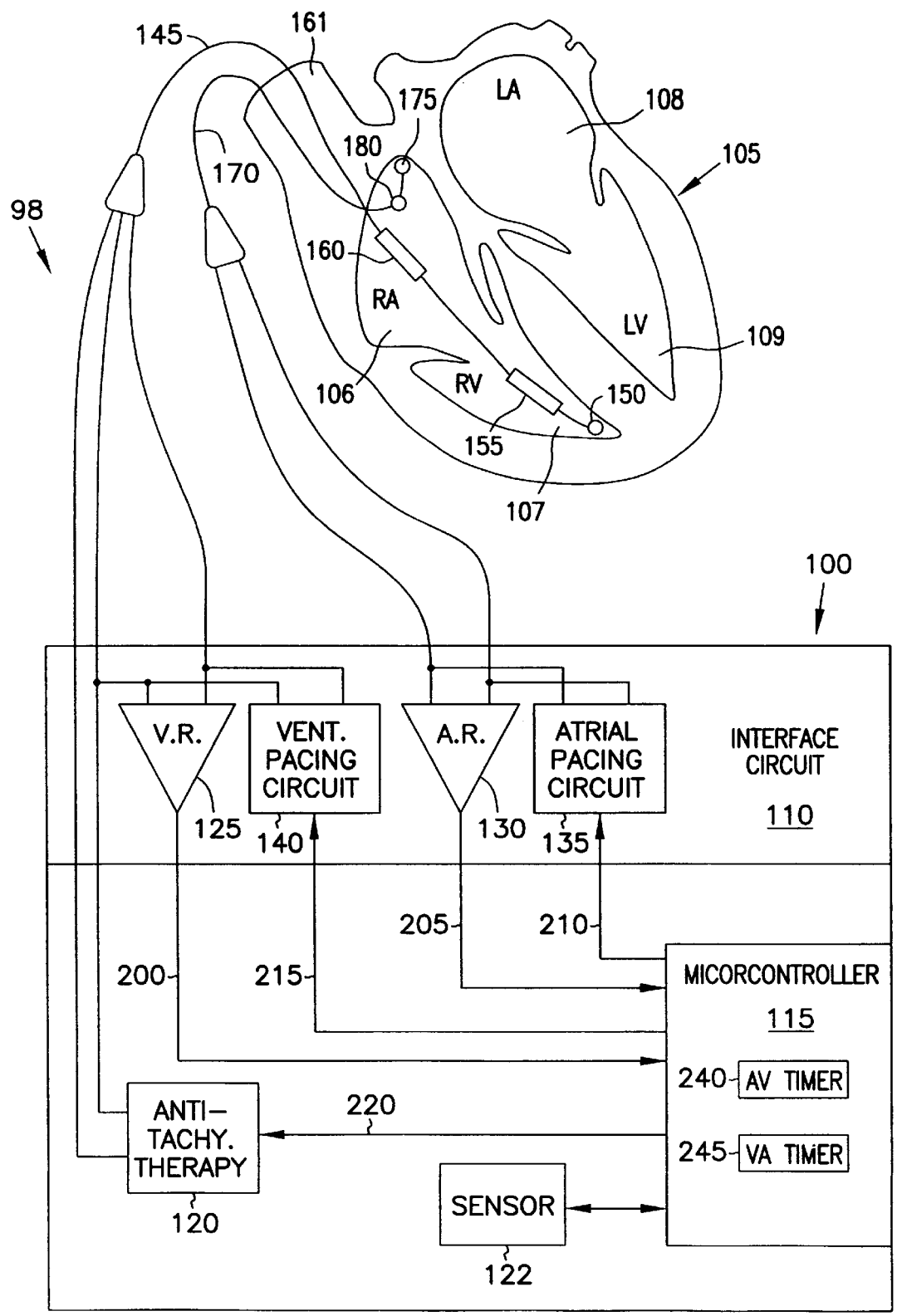
FIG. 2 is a schematic/block diagram illustrating generally one embodiment of a cardiac rhythm management system according to the present invention.

FIG. 2 is a schematic/block diagram illustrating generally one embodiment of a cardiac rhythm management system 98 according to the present invention, including implantable cardioverter-defibrillator (ICD) 100 and accompanying lead wires ("leads"), in relation to a heart 105 to which anti-tachyarrhythmia and other cardiac therapy is delivered. The heart 105 includes right atrium 106, right ventricle 107, left atrium 108, and left ventricle 109. ICD 100 includes an interface circuit 110, which conveys signals, including at least one heart activity signal, between ICD 100 and the heart 105. A microcontroller 115 processes heart activity signals received from the heart 105 and triggers the delivery of anti-tachyarrhythmia and other cardiac therapy. An anti-tachyarrhythmia therapy circuit 120 provides anti-tachyarrhythmia therapy to the heart 105.

One embodiment of ICD 100 includes a sensor 122 that determines whether the rate of pacing therapy delivered to the patient should be increased. Sensor 122 optionally includes an accelerometer that senses the patient's motion and activity, and increases the heart rate accordingly. Alternatively, sensor 122 includes an impedance measurement circuit that measures heart impedance signals and extracts information for modulation of the heart rate. In fact, sensor 122 may include any other technique for adjusting the rate of delivery of pacing pulses to the patient according to physiological and hemodynamic needs.

Interface circuit 110 includes a ventricular receiver 125 that receives a ventricular heart activity signal. An atrial receiver 130 receives an atrial heart activity signal. An atrial pacing circuit 135 provides atrial pacing therapy to an atrium, such as right atrium 106, of the heart 105. A ventricular pacing circuit 140 provides ventricular pacing therapy to a ventricle, such as right ventricle 107, of the heart 105.

Cardiac rhythm management system 98 includes both ICD 100 and leads that electrically couple ICD 100 to the heart 105. In one embodiment, ICD 100 is electrically coupled to the heart 105, such as through a tri-conductor first lead 145, which typically comprises a distal electrode 150, an intermediate electrode 155, and a proximal electrode 160. In this embodiment of cardiac rhythm management system 98, distal electrode 150 is typically located near an apex of right ventricle 107, intermediate electrode 155 is typically located in right ventricle 107, and proximal electrode 160 is typically located in right atrium 106 or in superior vena cava 161. In this embodiment of cardiac rhythm management system 98, ventricular pacing circuit 140 provides pacing stimuli to right ventricle 107, such as bipolar pacing pulses provided between distal electrode 150 and intermediate electrode 155. Ventricular receiver 125 senses a ventricular heart activity signal, such as by sensing between distal electrode 150 and intermediate electrode 155.

ICD 100 is also electrically coupled to the heart 105, such as through a dual conductor second lead 170, which typically comprises a distal atrial electrode, such as tip electrode 175, and a proximal atrial electrode, such as ring electrode 180. In this embodiment of cardiac rhythm management system 98, atrial pacing circuit 135 provides pacing stimuli to right atrium 106, such as by providing bipolar pacing pulses between tip electrode 175 and ring electrode 180, each located in right atrium 106 of the heart 105. As illustrated in FIG. 2, cardiac rhythm management system 98 includes ICD 100, first lead 145, and second lead 170.

Anti-tachyarrhythmia therapy circuit 120 provides anti-tachyarrhythmia therapy, such as an electrical countershock or anti-tachycardia pacing pulses, or triggers anti-tachyarrhythmia drug delivery to the heart. In this embodiment of cardiac rhythm management system 98, anti-tachyarrhythmia therapy circuit 120 provides an electrical countershock to the heart, such as between intermediate electrode 155 and proximal electrode 160.

Microcontroller 115 receives a ventricular heart activity signal through node/bus 200 from ventricular receiver 125. Microcontroller 115 also receives an atrial heart activity signal through node/bus 205 from atrial receiver 130. Microcontroller 115 uses such heart activity signals to determine when atrial and ventricular pacing stimuli are needed. Microcontroller 115 triggers, through at least one control signal at node/bus 210, the delivery by atrial pacing circuit 135 of atrial pacing stimuli to right atrium 106. Microcontroller 115 also triggers, through at least one control signal at node/bus 215, the delivery by ventricular pacing circuit 140 of ventricular pacing stimuli to right ventricle 107. Microcontroller 115 also triggers, through at least one control signal at node/bus 220, the delivery by anti-tachyarrhythmia therapy circuit 120 of anti-tachyarrhythmia therapy to heart 105.

Microcontroller 115 triggers the delivery of pacing and anti-tachyarrhythmia therapies to the heart in such a manner that the risk of inappropriate delivery of anti-tachyarrhythmia therapy is reduced. Microcontroller 115 typically includes an AV timer 240 that measures an atrial-ventricular (AV) time interval initiated upon an atrial event, as described in detail below. Microcontroller 115 also typically includes a VA timer 245 that measures a ventricular-atrial (VA) time interval initiated upon a ventricular event, also described in detail below. AV timer 240 and VA timer 245 may be implemented as a hardware counter, a sequence of instructions performed on a microprocessor such as microcontroller 115, or any other suitable timer implementation.

Figure 3:
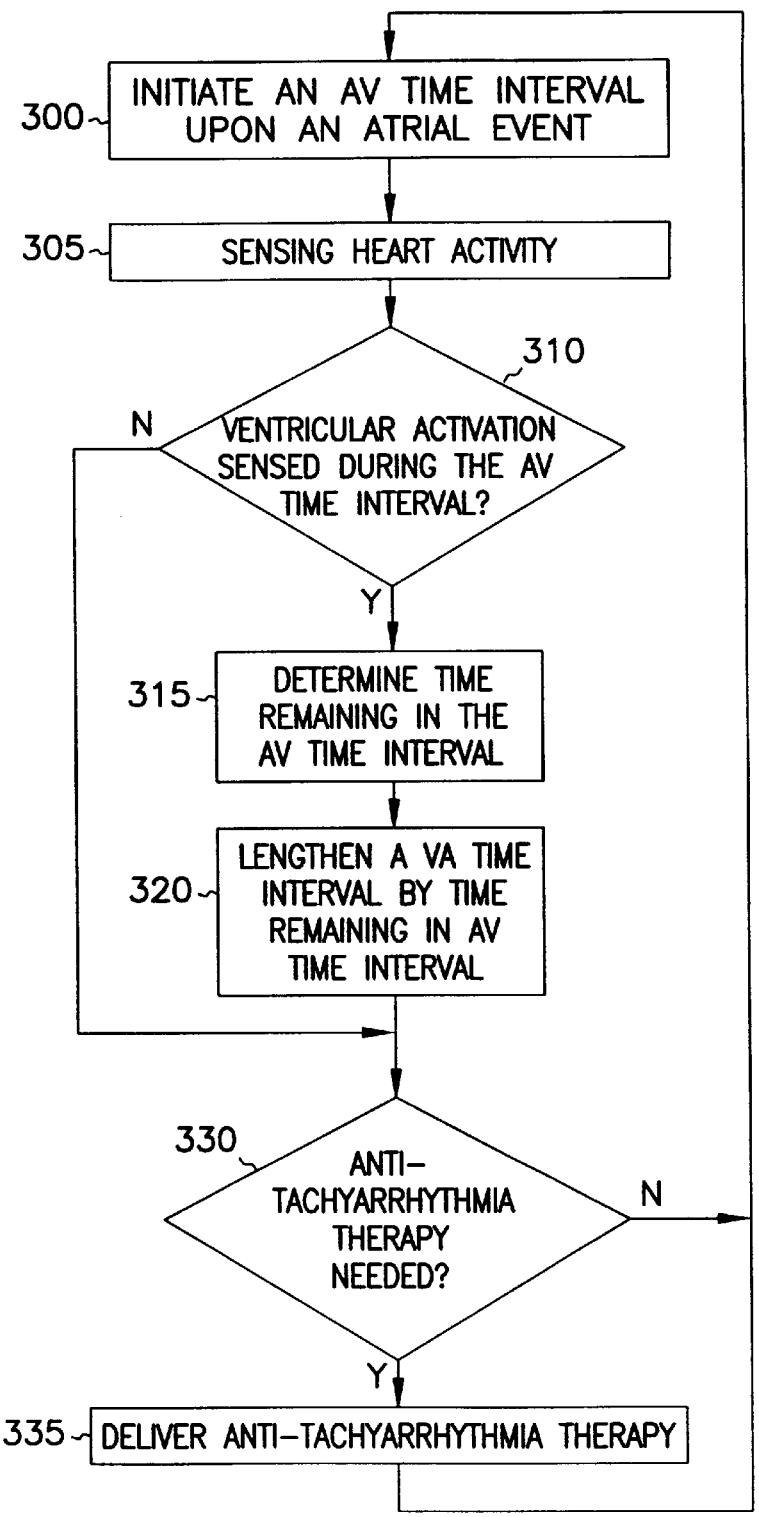
FIG. 3 is a flow chart illustrating generally one embodiment of a method of applying anti-tachyarrhythmia therapy to a heart according to the present invention.

FIG. 3 is a flow chart illustrating generally one embodiment of a method of applying anti-tachyarrhythmia therapy to a heart according to the modified atrial-based timing technique included within the present invention. The method illustrated in FIG. 3 is understood to relate to the application of anti-tachyarrhythmia therapy by cardiac rhythm management device 98 or any other cardiac rhythm management device, and is particularly useful for the application of anti-tachyarrhythmia therapy that includes an electrical countershock delivered by ICD 100 or other implantable cardioverter-defibrillator. As described above, this method advantageously triggers the delivery of pacing and anti-tachyarrhythmia therapy to the heart in such a manner that the risk of inappropriate delivery of anti-tachyarrhythmia therapy is reduced.

In FIG. 3 at step 300, an AV time interval is initiated upon an atrial event. The atrial event may be an intrinsic atrial activation that is sensed, for example, by atrial receiver 130 from electrical signals detected between tip electrode 175 and ring electrode 180. The atrial event may also comprise the delivery of an atrial pacing stimulus. Upon the occurrence of either such species of the atrial event, an AV time interval is initiated at step 300, such as by resetting AV timer 240, which subsequently measures elapsed time.

At step 305, heart activity is sensed, for example, by ventricular receiver 125 from electrical signals detected between distal electrode 150 and intermediate electrode 155. At step 310, if the sensed heart activity includes a ventricular activation sensed during the AV time interval (i.e., the ventricular activation occurs before the elapsed time measured by AV timer 240 reaches an adjustably programmable AV time interval value), then two steps conditionally follow.

First, a determination is made at step 315 of the time remaining in the AV time interval subsequent to the ventricular activation sensed therein. This determination may be made by taking the difference between the AV time interval value and the elapsed time measured by AV timer 240. Alternatively, AV timer 240 counts down from the AV time interval value, so that the time remaining in the AV time interval may be obtained by reading AV timer 240 directly. Second, the VA time interval is lengthened at step 320, for that particular cardiac cycle, by the time remaining in the AV time interval subsequent to the ventricular activation sensed therein. In other words, the VA time interval is lengthened by the difference in time between the occurrence of the sensed ventricular activation and the time at which a ventricular pacing pulse would have been delivered had no ventricular activation been sensed during the AV time interval. This increases the time delay before an atrial pacing stimulus will be delivered if no intervening atrial activation is sensed.

The method of FIG. 3 also determines, at step 330, whether the heart activity, such as that sensed in step 305, indicates a need for anti-tachyarrhythmia therapy. Sensed heart activity indicating a need for anti-tachyarrhythmia therapy may include, for example, sustained monomorphic or polymorphic ventricular tachycardia, or ventricular fibrillation. Appropriate anti-tachyarrhythmia therapy is delivered at step 335, depending on the type of indication detected at step 330. For example, ICD 100 may deliver a low energy cardioversion electrical countershock to convert an episode of ventricular tachycardia into a normal cardiac rhythm. In another example, ICD 100 may deliver a higher energy defibrillation electrical countershock to convert an episode of ventricular fibrillation into a normal cardiac rhythm. ICD 100 typically continues to provide anti-tachyarrhythmia therapy at step 335 until a normal cardiac rhythm is obtained, at which time the method of operation of the system continues at step 300 upon an atrial event, as described above.

Figure 4:
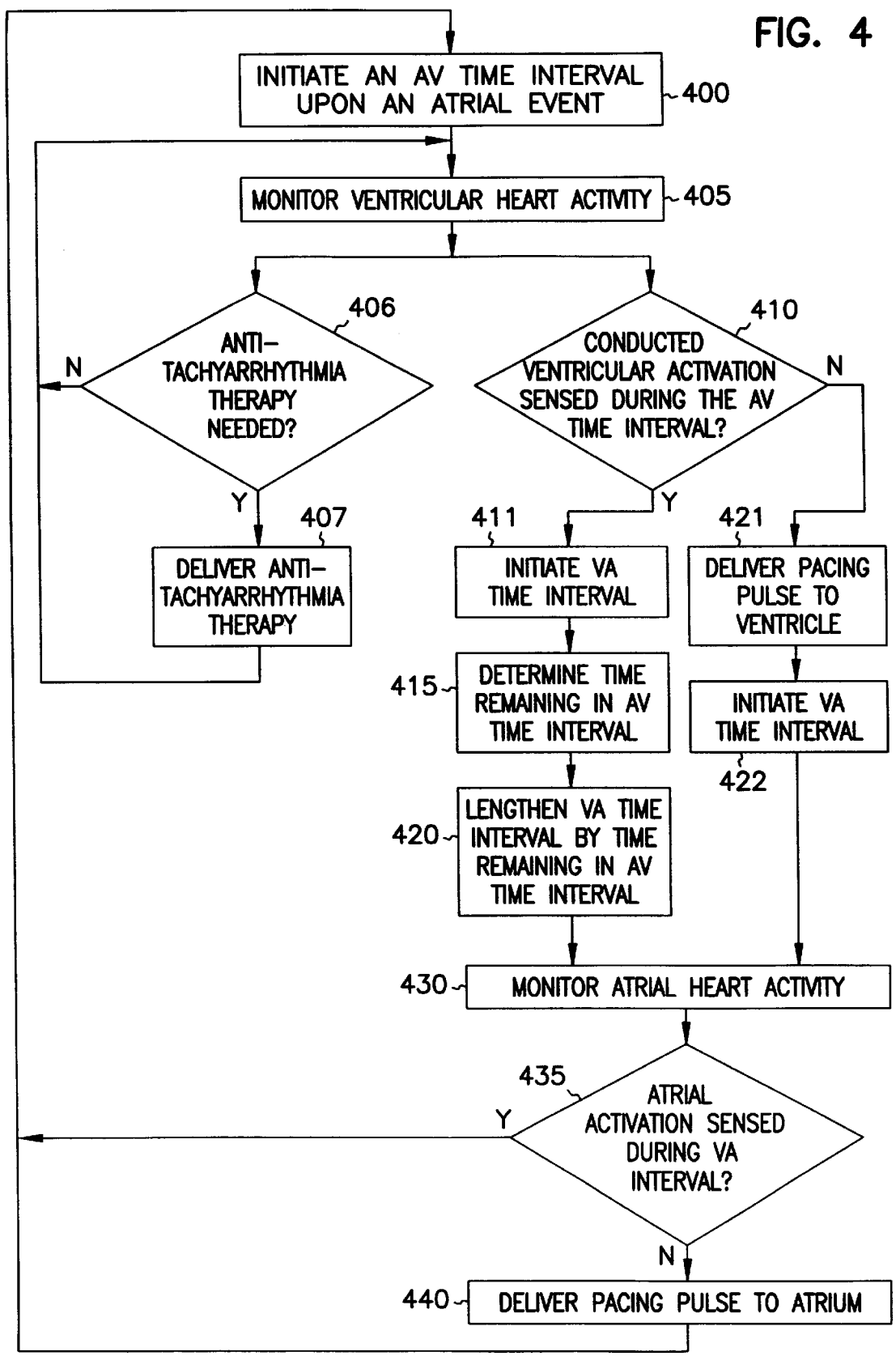
FIG. 4 is a more detailed flow chart illustrating generally one embodiment of a method of applying pacing and antitachyarrhythmia therapy to a heart according to the present invention.

FIG. 4 is a more detailed flow chart illustrating generally one embodiment of a method of applying pacing and anti-tachyarrhythmia therapy to a heart according to the modified atrial-based timing technique included within the present invention. The method illustrated in FIG. 4 is understood to relate to the application of anti-tachyarrhythmia therapy by any cardiac rhythm management device, and is particularly useful for the application of anti-tachyarrhythmia therapy that includes an electrical countershock delivered by an implantable cardioverter-defibrillator such as ICD 100. As described above, this method advantageously includes triggering the delivery of pacing and anti-tachyarrhythmia therapies to the heart 105 in such a manner that the risk of inappropriate delivery of anti-tachyarrhythmia therapy is reduced.

At step 400, an AV time interval is initiated upon an atrial event. The atrial event may be an intrinsic atrial activation that is sensed, for example, by atrial receiver 130 from electrical signals detected between tip electrode 175 and ring electrode 180. The atrial event may also comprise the delivery of an atrial pacing stimulus. Upon the occurrence of either such species of atrial event, an AV time interval is initiated, such as by resetting AV timer 240, which subsequently measures elapsed time.

At step 405, ventricular heart activity is sensed, for example, by ventricular receiver 125 from electrical signals detected between distal electrode 150 and intermediate electrode 155. At step 406, a determination is made, such as by microcontroller 115 based upon the sensed ventricular heart activity of step 405, of whether anti-tachyarrhythmia therapy is needed. If no anti-tachyarrhythmia therapy is needed, the monitoring of ventricular heart activity is continued at step 405. If anti-tachyarrhythmia therapy is needed at step 406, it is delivered at step 407, before the monitoring of ventricular heart activity is continued at step 405.

At step 410, if the sensed ventricular heart activity includes a ventricular activation sensed during the AV time interval (i.e., the ventricular activation occurs before the elapsed time, measured by AV timer 240, reaches an adjustably programmable AV time interval value), then three steps conditionally follow. First, a VA time interval is initiated at step 411, such as by resetting VA timer 245, which subsequently measures elapsed time. Second, a determination is made at step 415 of the time remaining in the AV time interval subsequent to the ventricular activation sensed therein. This determination may be made by taking the difference between the AV time interval value and the elapsed time measured by AV timer 240. Alternatively, AV timer 240 counts down from the AV time interval value, so that the time remaining in the AV time interval may be obtained by reading AV timer 240 directly. Third, the VA time interval is lengthened, for that particular cardiac cycle, at step 420 by the time remaining in the AV time interval subsequent to the ventricular activation sensed during the AV time interval. In other words, the VA time interval is lengthened by the difference in time between the occurrence of the sensed ventricular activation and the time at which a ventricular pacing pulse would have been delivered had no ventricular activation been sensed during the AV time interval. This increases the time delay before an atrial pacing stimulus will be delivered if no intervening atrial activation is sensed.

At step 410, if no conducted ventricular activation is sensed during the AV time interval, a pacing pulse is delivered to the ventricle at step 421, and the VA time interval is initiated at step 422, such as by resetting VA timer 245, which subsequently measures elapsed time.

At step 430, atrial heart activity is monitored, such as by atrial receiver 130 from electrical signals detected between tip electrode 175 and ring electrode 180. If an atrial activation is sensed at step 435 during the VA interval, the AV time interval is initiated at step 400, as described above. If no atrial activation is sensed during the VA time interval, a pacing pulse is delivered at step 440 to right atrium 106 before the AV time interval is initiated at step 400.

Figure 5:
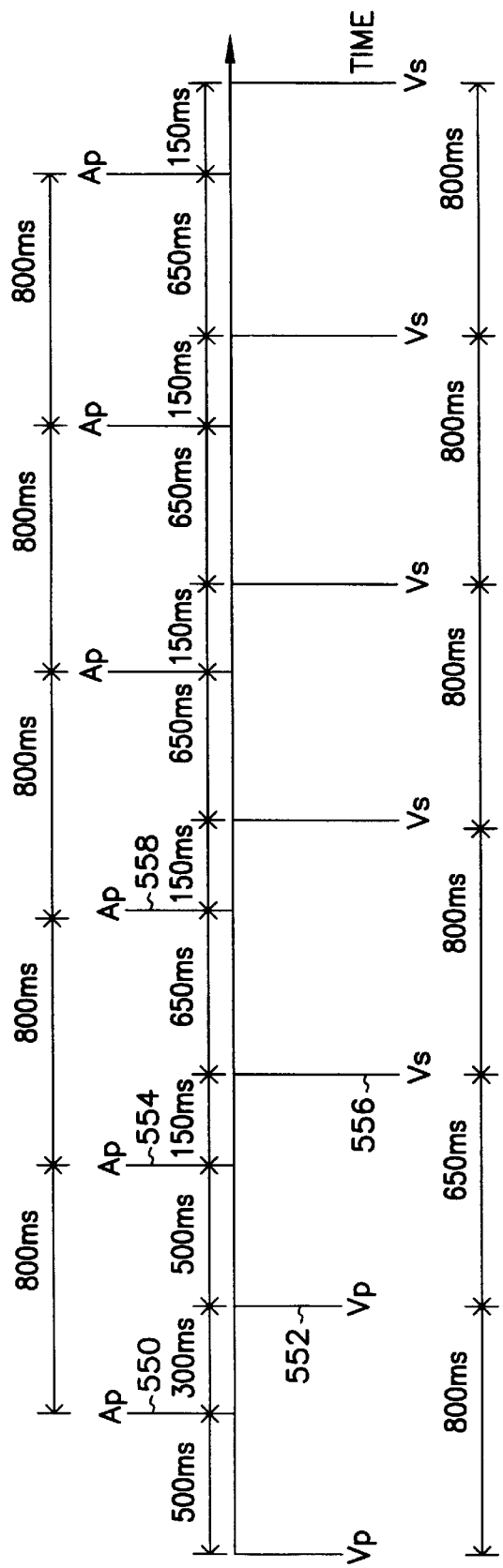
FIG. 5 is a timing diagram, of the same general type as that of FIG. 1, illustrating a scenario including some of the advantages of the device and method according to the present invention.

FIG. 5 is a timing diagram, of the same general type as that illustrated in FIG. 1, illustrating a scenario including some of the advantages of the device and method according to the present invention. In the example of FIG. 5, a defibrillator, such as ICD 100, is programmed to provide pacing pulses to a particular chamber of the heart at a rate of 75 beats per minute, corresponding to an 800 millisecond time interval between pulses to a particular chamber of the heart. The defibrillator is also programmed to have an AV time interval of 300 milliseconds, i.e. delivery of a ventricular pulse is delayed from delivery of the previous atrial pulse by the AV time interval of 300 milliseconds. In FIG. 5, the VA time interval has a default value of 500 milliseconds but, according to the present system, the actual value of the VA time interval varies, as described above. The defibrillator is also programmed to inhibit delivery of a pacing pulse when an intrinsic activation of the heart is sensed.

In FIG. 5, a first pulse 550 is delivered to right atrium 106, thereby also initiating a 300 millisecond AV time interval. A second pulse 552 is delivered to right ventricle 107 at 300 milliseconds after the delivery of first pulse 550, since no ventricular activation was sensed during the AV time interval initiated by first pulse 550. The delivery of second pulse 552 also initiates a 500 millisecond VA time interval. A third pulse 554 is delivered to the atrium 500 milliseconds after the delivery of second pulse 552, since no atrial activation was sensed during the VA time interval initiated by second pulse 552. Subsequent events in the timing diagram of FIG. 5 illustrate a possible condition in which electrical conduction through physiological pathways from the atrium to the ventricle is faster than the 300 millisecond AV time interval.

For example, with such fast conduction between the atrium and the ventricle, the delivery of third pulse 554 may result in a conducted intrinsic first ventricular activation 556 that is sensed 150 milliseconds after the delivery of third pulse 554, i.e. during the 300 millisecond AV time interval initiated by the delivery of third pulse 554. The sensed ventricular activation 556 initiates a VA time interval having a default value of 500 milliseconds. According to the present system, however, the value of the VA time interval is increased from the default value by the time remaining in the AV time interval following the sensed ventricular activation 556. Since the AV time interval had 150 milliseconds remaining when ventricular activation 556 was sensed, the VA time interval initiated by sensed ventricular activation 556 is increased by 150 milliseconds from its default value of 500 milliseconds. Thus, the value of the VA time interval initiated by sensed ventricular activation 556 is increased to 650 milliseconds. If no intervening atrial activation is sensed during the VA time interval, atrial pace pulse 558 is delivered 650 milliseconds after ventricular activation 556 is sensed, as illustrated in FIG. 5. As a result, the time interval between pulses to a particular chamber of the heart, e.g. the time interval between atrial pace pulse 554 and atrial pace pulse 558, remains at 800 milliseconds, and is not elevated due to the sensing of a ventricular activation during the AV time interval.

FIG. 5 illustrates the possibility of similar subsequent sensed ventricular activations, each occurring within the 300 millisecond AV time interval initiated by the previous atrial pace pulse, due to the fast electrical conduction between the atrium and ventricle of the heart. According to the present invention, each VA interval is increased by the time remaining in the immediately preceding AV time interval after a ventricular activation is sensed therein. This advantageously maintains the heart rate at its programmed value of 75 beats per minute, corresponding to 800 milliseconds between atrial events or between ventricular events, notwithstanding ventricular activations sensed during the AV time interval. Since heart rate is not elevated due to the sensing of a ventricular activation during the AV time interval, the risk of inappropriate delivery of anti-tachyarrhythmia therapy is reduced.

Though the invention has been described above with respect to the fixed-rate delivery of pacing therapy, it is understood to also apply to the delivery of pacing therapy in which the pacing delivery rate is modulated, such as by a sensor in response to physiological or other indications that the heart rate should be varied. In such a rate-responsive system, the AV and VA time intervals, either individually or in combination, may be shortened for a particular cardiac cycle from default lower rate limit values in response to sensor indications that the heart rate should be increased. The shortened values of the AV and VA time intervals are sometimes referred to as the sensor-driven AV and VA time interval values, and the heart rate indicated by the sensor is sometimes referred to as the sensor-driven rate. In such a case, operation of the present invention is similar to the above-description, however, sensor-driven AV and VA time interval values are used so that the sensor-driven rate is not further elevated by ventricular activations that are sensed during the sensor-driven AV time interval.

Figure 6:
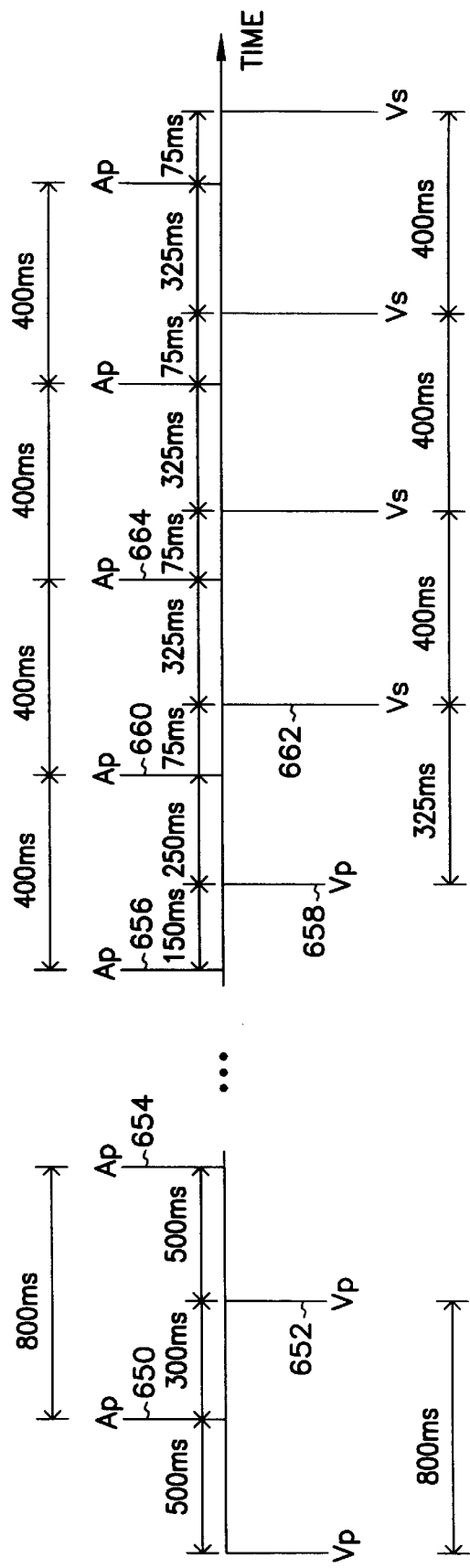
FIG. 6 is a timing diagram, of the same general type as that of FIG. 5, illustrating a scenario including some of the advantages of the device and method according to a first rate-responsive embodiment of the present invention.

FIG. 6 is a timing diagram, of the same general type as that of FIG. 5, illustrating one scenario of one embodiment of the present system's operation when the heart rate is increased in response to physiological or other sensor indications. In the example of FIG. 6, the defibrillator is programmed to provide pacing pulses to a particular chamber of the heart at a lower rate of 75 beats per minute, corresponding to an 800 millisecond maximum time interval between pulses to a particular chamber of the heart. However, the sensor-driven rate may exceed the lower rate in response to sensor indications.

The defibrillator is also programmed to have an maximum AV time interval of 300 milliseconds, i.e. the delivery of a ventricular pulse is delayed from the delivery of the atrial pulse by the sensor-driven AV time interval, which does not exceed 300 milliseconds. In FIG. 6, the maximum VA time interval has a default value of 500 milliseconds. The sensor-driven VA time interval may be shortened in response to sensor indications, and may be lengthened, according to the present system, in response to ventricular activations that are sensed during the sensor-driven AV time interval. The defibrillator is also programmed to inhibit delivery of a pacing pulse when an intrinsic activation of the heart is sensed.

In FIG. 6, a first pulse 650, a second pulse 652, and a third pulse 654 illustrate operation of the present system at the lower rate, i.e. when the sensor does not indicate that heart rate should be increased above the lower rate value. First pulse 650 is delivered to right atrium 106, thereby also initiating a 300 millisecond AV time interval. A second pulse 652 is delivered to right ventricle 107 at 300 milliseconds after the delivery of first pulse 650, since no ventricular activation was sensed during the AV time interval initiated by first pulse 650. The delivery of second pulse 652 also initiates a 500 millisecond VA time interval. A third pulse 654 is delivered to the atrium 500 milliseconds after the delivery of second pulse 652, since no atrial activation was sensed during the AV time interval initiated by second pulse 652.

The subsequent events that follow the broken line in the time axis of FIG. 6 illustrate, by way of example only, a condition in which the sensor indicates that the heart rate should be increased to a sensor-driven rate of 150 beats per minute, corresponding to a time interval of 400 milliseconds between pulses to a particular chamber of the heart. This example illustrates one embodiment of the present invention in which the sensor-driven AV and VA time intervals are both reduced proportionately, such that the sensor-driven AV time interval is 150 milliseconds and the sensor-driven VA time interval is 250 milliseconds.

In FIG. 6, a fourth pulse 656, a fifth pulse 658, and a sixth pulse 660 illustrate operation of the present invention at the sensor-driven rate of 150 beats per minute. Fourth pulse 656 is delivered to right atrium 106, thereby also initiating a 150 millisecond sensor-driven AV time interval. Fifth pulse 658 is delivered to right ventricle 107 at 150 milliseconds after the delivery of fourth pulse 656, since no ventricular activation was sensed during the sensor-driven AV time interval initiated by fourth pulse 656. The delivery of fifth pulse 658 also initiates a 250 millisecond sensor-driven VA time interval. Sixth pulse 660 is delivered to the atrium 250 milliseconds after the delivery of fifth pulse 658, since no atrial activation was sensed during the sensor-driven VA time interval initiated by fifth pulse 658. Subsequent events in the timing diagram of FIG. 6 illustrate a possible condition in which electrical conduction through physiological pathways from the atrium to the ventricle is faster than the 150 millisecond sensor-driven AV time interval.

For example, with such fast conduction between the atrium and the ventricle, the delivery of sixth pulse 660 may result in a conducted intrinsic first ventricular activation 662 that is sensed 75 milliseconds after the delivery of sixth pulse 660, i.e. during the 150 millisecond sensor-driven AV time interval initiated by the delivery of sixth pulse 660. The sensed ventricular activation 662 initiates a sensor-driven VA time interval having a default value of 250 milliseconds. According to this embodiment of FIG. 6, however, the value of the sensor-driven VA time interval is increased from the default value by the time remaining in the sensor-driven AV time interval following the sensed ventricular activation 662. Since the sensor-driven AV time interval had 75 milliseconds remaining when ventricular activation 662 was sensed, the sensor-driven VA time interval initiated by sensed ventricular activation 662 is increased by 75 milliseconds from its default value of 250 milliseconds. Thus, the value of the sensor-driven VA time interval initiated by sensed ventricular activation 662 is increased to 325 milliseconds. If no intervening atrial activation is sensed during the sensor-driven VA time interval, atrial pace pulse 664 is delivered 325 milliseconds after ventricular activation 662 is sensed, as illustrated in FIG. 6. As a result, the time interval between pulses to a particular chamber of the heart, e.g. the time interval between atrial pace pulse 660 and atrial pace pulse 664, remains at the sensor-driven value of 400 milliseconds, and is not elevated due to the sensing of a ventricular activation during the sensor-driven AV time interval.

FIG. 6 also illustrates the possibility of similar subsequent sensed ventricular activations, each occurring within the 150 millisecond sensor-driven AV time interval initiated by the previous atrial pace pulse, due to the fast electrical conduction between the atrium and ventricle of the heart. According to the present system, each sensor-driven VA interval is increased by the time remaining in the immediately preceding sensor-driven AV time interval after a ventricular activation is sensed therein. This advantageously maintains the heart rate at its sensor-driven value of 150 beats per minute, corresponding to 400 milliseconds between atrial events or between ventricular events, notwithstanding ventricular activations sensed during the sensor-driven AV time interval. Since the heart rate is not elevated due to the sensing of a ventricular activation during the sensor-driven AV time interval, the risk of inappropriate delivery of anti-tachyarrhythmia therapy is reduced. More particularly, the system avoids the inappropriate delivery of anti-tachyarrhythmia therapy due to a fast rate of the delivery of atrial paces that are conducted to the ventricle, sensed as a fast sequence of ventricular events, and trigger delivery of the anti-tachyarrhythmia therapy.

Figure 7:
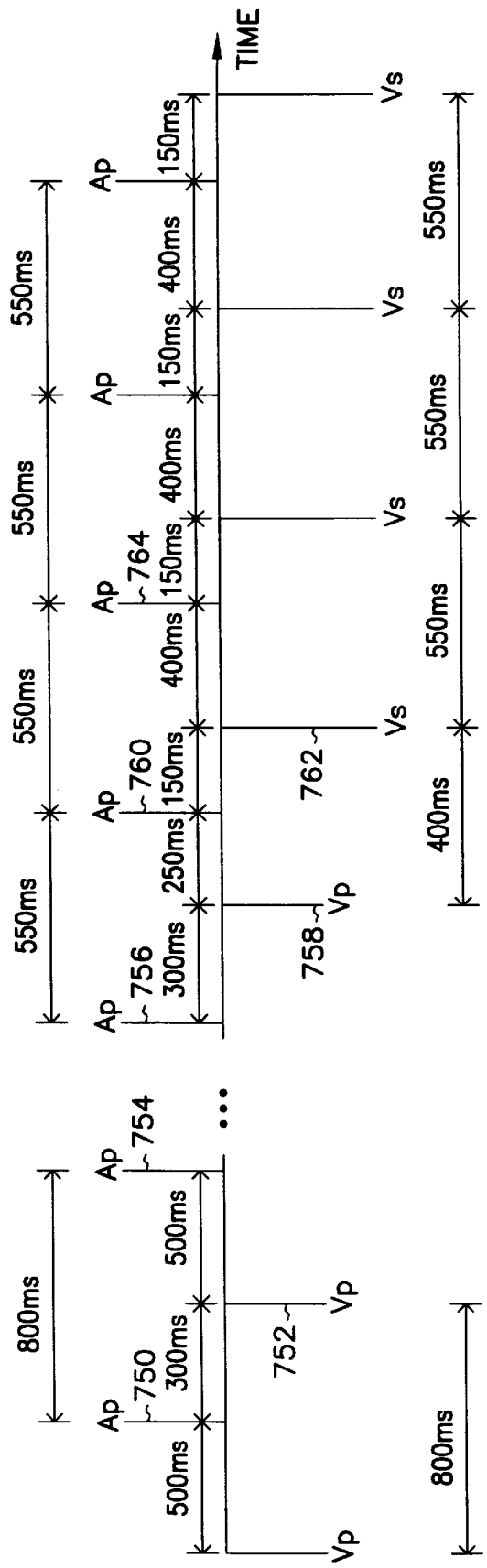
FIG. 7 is a timing diagram, of the same general type as that of FIG. 6, illustrating a scenario including some of the advantages of the device and method according to a second rate-responsive embodiment of the present invention.

FIG. 7 is a timing diagram, of the same general type as that of FIG. 6, illustrating a scenario of another embodiment of the present invention's operation in which the heart rate is increased in response to physiological or other sensor indications. In the example of FIG. 7, the defibrillator is programmed to provide pacing pulses to a particular chamber of the heart at a lower rate of 75 beats per minute, corresponding to an 800 millisecond maximum time interval between pulses to a particular chamber of the heart. However, the sensor-driven rate may exceed the lower rate in response to sensor indications. In the embodiment of FIG. 7, the AV time interval is not modulated in response to sensor indications; only the VA time interval is modulated in response to sensor indications.

The defibrillator is also programmed to have an AV time interval of 300 milliseconds, i.e. the delivery of a ventricular pulse is delayed from the delivery of the atrial pulse by the AV time interval of 300 milliseconds. In FIG. 7, the maximum VA time interval has a default value of 500 milliseconds. The sensor-driven VA time interval may be shortened in response to sensor indications, and may be lengthened, according to the present system, in response to ventricular activations that are sensed during the AV time interval. The defibrillator is also programmed to inhibit delivery of a pacing pulse when an intrinsic activation of the heart is sensed.

In FIG. 7, a first pulse 750, a second pulse 752, and a third pulse 754 illustrate operation of the present invention at the lower rate, i.e. the sensor does not indicate that heart rate should be increased above the lower rate value. First pulse 750 is delivered to right atrium 106, thereby also initiating a 300 millisecond AV time interval. Second pulse 752 is delivered to right ventricle 107 at 300 milliseconds after the delivery of first pulse 750, since no ventricular activation was sensed during the AV time interval initiated by first pulse 750. The delivery of second pulse 752 also initiates a 500 millisecond VA time interval. Third pulse 754 is delivered to the atrium 500 milliseconds after the delivery of second pulse 752, since no atrial activation was sensed during the AV time interval initiated by second pulse 752.

The subsequent events that follow the broken line in the time axis of FIG. 7 illustrate, by way of example only, a condition in which the sensor indicates that the heart rate should be increased to a sensor-driven rate of approximately 109 beats per minute, corresponding to a time interval of 550 milliseconds between pulses to a particular chamber of the heart. This example illustrates one embodiment of the present invention in which only the VA time interval is shortened in response to sensor indications, such that the AV time interval remains at 300 milliseconds, but the sensor-driven VA time interval is reduced to 250 milliseconds if no intervening ventricular activation is sensed during the AV time interval.

In FIG. 7, a fourth pulse 756, a fifth pulse 758, and a sixth pulse 760 illustrate operation of the present invention at the sensor-driven rate of approximately 109 beats per minute. Fourth pulse 756 is delivered to right atrium 106, thereby also initiating a 300 millisecond AV time interval. Fifth pulse 758 is delivered to right ventricle 107 at 300 milliseconds after the delivery of fourth pulse 756, since no ventricular activation was sensed during the AV time interval initiated by fourth pulse 756. The delivery of fifth pulse 758 also initiates a 250 millisecond sensor-driven VA time interval. Sixth pulse 760 is delivered to the atrium 250 milliseconds after the delivery of fifth pulse 758, since no atrial activation was sensed during the sensor-driven VA time interval initiated by fifth pulse 758. Subsequent events in the timing diagram of FIG. 7 illustrate a possible condition in which electrical conduction through physiological pathways from the atrium to the ventricle is faster than the 300 millisecond AV time interval.

For example, with such fast conduction between the atrium and the ventricle, the delivery of sixth pulse 760 may result in a conducted intrinsic first ventricular activation 762 that is sensed 150 milliseconds after the delivery of sixth pulse 760, i.e. during the 300 millisecond AV time interval initiated by the delivery of sixth pulse 760. The sensed ventricular activation 762 initiates a sensor-driven VA time interval having a default value of 250 milliseconds. In the embodiment of FIG. 7, however, the value of the sensor-driven VA time interval is increased from the default value by the time remaining in the AV time interval following the sensed ventricular activation 762. Since the AV time interval had 150 milliseconds remaining when ventricular activation 762 was sensed, the sensor-driven VA time interval initiated by sensed ventricular activation 762 is increased by 150 milliseconds from its default value of 250 milliseconds.

Thus, the value of the sensor-driven VA time interval initiated by sensed ventricular activation 762 is increased to 400 milliseconds. If no intervening atrial activation is sensed during the sensor-driven VA time interval, atrial pace pulse 764 is delivered 400 milliseconds after ventricular activation 762 is sensed, as illustrated in FIG. 7. As a result, the time interval between pulses to a particular chamber of the heart, e.g. the time interval between atrial pace pulse 760 and atrial pace pulse 764, remains at the sensor-driven value of 550 milliseconds, and is not elevated due to the sensing of a ventricular activation during the AV time interval.

FIG. 7 also illustrates the possibility of similar subsequent sensed ventricular activations, each occurring within the 300 millisecond AV time interval initiated by the previous atrial pace pulse, due to the fast electrical conduction between the atrium and ventricle of the heart. According to the present system, each sensor-driven VA interval is increased by the time remaining in the immediately preceding AV time interval after a ventricular activation is sensed therein. This advantageously maintains the heart rate at its sensor-driven value of approximately 109 beats per minute, corresponding to 550 milliseconds between atrial events or between ventricular events, notwithstanding ventricular activations sensed during the AV time interval. Since heart rate is not elevated due to the sensing of a ventricular activation during the AV time interval, the risk of inappropriate delivery of anti-tachyarrhythmia therapy is reduced.

Thus, the present system recognizes that the delivery of pacing therapy may, under certain conditions, result in inappropriate delivery of anti-tachyarrhythmia therapy. The present system includes a modified atrial-based timing device and method that provides pacing and anti-tachyarrhythmia therapies to the heart such that the risk of inappropriate delivery of anti-tachyarrhythmia therapy is advantageously reduced.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of cardiac rhythm management, comprising the steps of:
   restricting ventricular and atrial pacing therapy to a variable ventricular-atrial (VA) time interval therapy, when an electrical countershock therapy is enabled, the VA time interval therapy comprising the steps of:
   (a) initiating an atrial-ventricular (AV) time interval upon an atrial event;
   (b) sensing heart activity including a ventricular activation during the AV time interval;
   (c) determining a time remaining in the AV time interval subsequent to the ventricular activation sensed during the AV time interval; and
   (d) lengthening a ventricular-atrial (VA) time interval by the time remaining in the AV time interval as determined in step (c);
   determining if the sensed heart activity indicates a need for delivering an electrical countershock; and
   delivering the electrical countershock, if needed.

2. The method of claim 1, wherein the atrial event comprises a pacing pulse delivered to the atrium of the heart.

3. The method of claim 1, wherein the atrial event comprises a sensed intrinsic atrial activation of the heart.

4. A method of applying pacing and electrical countershock therapies to a heart such that the risk of an inappropriate electrical countershock is reduced, the method comprising the steps of:
   restricting ventricular and atrial pacing therapy to a variable ventricular-atrial (VA) time interval therapy, when the electrical countershock therapy is enabled, the VA time interval therapy comprising the steps of:
   (a) initiating an atrial-ventricular (AV) time interval upon an atrial event;
   (b) monitoring ventricular heart activity of a ventricle of the heart, including monitoring for a conducted ventricular activation during the AV time interval;
   (c) determining a time remaining in the AV time interval if the conducted ventricular activation is sensed during the AV time interval;
   (d) delivering a pacing pulse to the ventricle after the AV time interval if no conducted ventricular activation is sensed during the AV time interval;
   (e) initiating a ventricular-atrial (VA) time interval upon a ventricular event, the step of initiating a VA time interval comprising both sensing of the conducted ventricular activation during the AV time interval and also delivering the pacing pulse to the ventricle after the AV time interval if no conducted ventricular activation is sensed during the AV time interval; and
   (f) lengthening the VA time interval by the time remaining in step (c) in the AV time interval if the conducted ventricular activation is sensed during the AV time interval;
   determining if the sensed heart activity indicates a need for delivering an electrical countershock; and
   delivering the electrical countershock, if needed.

5. The method of claim 4, wherein the atrial event comprises a pacing pulse delivered to the atrium of the heart.

6. The method of claim 4, wherein the atrial event comprises a sensed intrinsic atrial activation of the heart.

7. A cardiac rhythm management device receiving a heart activity signal from a heart and applying electrical countershock therapy to the heart, the device comprising:
   an interface circuit for receiving the heart activity signal and delivering the electrical countershock therapy;
   a microcontroller, coupled to the interface circuit for detecting atrial and ventricular events based on the heart activity signal, the microcontroller restricting ventricular and atrial pacing therapy to a variable ventricular-atrial (VA) time interval therapy when electrical countershock therapy is enabled, the VA time interval therapy including initiating an atrial-ventricular (AV) time interval upon one of the atrial events and a ventricular-atrial (VA) time interval upon one of the ventricular events, wherein said microprocessor determines a time remaining in the AV time interval subsequent to the ventricular events sensed during the AV time interval and lengthens the VA time interval by the determined time, and the microcontroller determines if the heart activity signal indicates a need for an electrical countershock; and an electrical countershock therapy circuit, responsive to the microcontroller determining if the heart activity signal indicates a need for an electrical countershock, to generate the electrical countershock to be delivered to the heart by the interface circuit.

8. The device of claim 7, wherein the VA time interval is lengthened, in response to one of the ventricular events comprising a ventricular activation sensed during the AV time interval, by the time remaining in the AV time interval subsequent to the sensed ventricular activation.

9. The device of claim 7, wherein the microcontroller, based upon the heart activity signal, triggers delivery of DDD pacing therapy by the interface circuit to the heart.

10. The device of claim 7, wherein the one of the atrial events comprises a pacing pulse delivered to the atrium of the heart.

11. The device of claim 7, wherein the one of the atrial events comprises a sensed intrinsic atrial activation of the heart.

12. The device of claim 7, wherein the interface circuit includes a ventricular receiver for receiving a ventricular heart activity signal from the ventricle of the heart.

13. The device of claim 7, wherein the interface circuit includes an atrial receiver for receiving an atrial heart activity signal from the atrium of the heart.

14. The device of claim 7, wherein the interface circuit includes a ventricular pulse circuit for providing an electrical pacing pulse to the ventricle of the heart.

15. The device of claim 7, wherein the interface circuit includes an atrial pulse circuit for providing an electrical pacing pulse to the atrium of the heart.

16. A cardiac rhythm management system receiving a heart activity signal applying electrical countershock therapy to the heart, the system comprising:

an atrial electrode;

a ventricular electrode;

an interface circuit coupled to each of the atrial and ventricular electrodes;

a microcontroller, coupled to the interface circuit for detecting atrial and ventricular events based on the heart activity signal, the microcontroller restricting ventricular and atrial pacing therapy to a variable ventricular-atrial (VA) time interval therapy when the electrical countershock therapy is enabled, the VA time interval therapy including initiating an atrial-ventricular (AV) time interval upon one of the atrial events and a ventricular-atrial (VA) time interval upon one of the ventricular events, wherein said microprocessor determines a time remaining in the AV time interval subsequent to the ventricular events sensed during the AV time interval and lengthens the VA time interval by the determined time, and the microcontroller determines if the heart activity signal indicates a need for an electrical countershock; and an electrical countershock circuit, responsive to the microcontroller determining if the heart activity signal indicates a need for providing an electrical countershock, to generate the electrical countershock to be delivered to the heart by the interface circuit.

17. The system of claim 16, wherein the VA time interval is lengthened, in response to the ventricular activation, if the ventricular activation is sensed during the AV time interval, by the time remaining in the AV time interval subsequent to the sensed ventricular activation.

18. The device of claim 16, wherein the microcontroller, based upon the heart activity signal, triggers delivery of DDD pacing therapy to the heart by the interface circuit.

19. The system of claim 16, wherein the one of the atrial events comprises a pacing pulse delivered to the atrium of the heart.

20. The system of claim 16, wherein the one of the atrial events comprises a sensed intrinsic atrial activation of the heart.

21. The system of claim 16, further comprising a lead carrying the atrial electrode.

22. The system of claim 16, further comprising a lead carrying the ventricular electrode.

23. The system of claim 16, wherein the system is implantable in a living organism.

24. The system of claim 16, wherein the interface circuit comprises:

an atrial pulse circuit, coupled to the atrial electrode, for providing pacing pulses to the atrium of the heart; and a ventricular pulse circuit, coupled to the ventricular electrode, for providing pacing pulses to the ventricle of the heart.

25. The system of claim 16, wherein the interface circuit comprises:

an atrial receiver, for receiving an atrial heart activity signal from the atrium of the heart; and a ventricular receiver, for receiving a ventricular heart activity signal from the ventricle of the heart.

\* \* \* \* \*